United States Patent
Wolf

(10) Patent No.: US 7,458,108 B2
(45) Date of Patent: Dec. 2, 2008

(54) SCENTED SINK STRAINER/STOPPER

(75) Inventor: Thomas H. Wolf, Highland Park, IL (US)

(73) Assignee: Bath Solutions, Inc., Bensenville, IL (US)

(*) Notice: Subject to any disclaimer, the term of this patent is extended or adjusted under 35 U.S.C. 154(b) by 660 days.

(21) Appl. No.: 11/169,355

(22) Filed: Jun. 29, 2005

(65) Prior Publication Data
US 2007/0000037 A1    Jan. 4, 2007

(51) Int. Cl.
*E03C 1/262* (2006.01)
(52) U.S. Cl. ............... 4/222.1; 4/222; 4/287; 4/290
(58) Field of Classification Search ....... 4/222, 4/222.1, 261, 287, 291, 292, 294, 309, 652; 422/266, 276; 210/163
See application file for complete search history.

(56) References Cited

U.S. PATENT DOCUMENTS

| | | | |
|---|---|---|---|
| 214,982 A * | 5/1879 | Atwater ............... 4/291 |
| 1,966,074 A * | 7/1934 | Fuld .................. 4/222.1 |
| 2,046,214 A * | 6/1936 | Selig ................. 4/222.1 |
| 2,225,693 A | 12/1940 | Frances |
| 2,569,615 A | 10/1951 | Link |
| 2,739,317 A | 3/1956 | Abresch |
| 3,104,400 A | 9/1963 | Lantz et al. |
| 3,596,294 A | 8/1971 | Hoffman |
| 3,813,708 A | 6/1974 | Hamburg |
| 3,902,877 A | 9/1975 | Swaim |
| 3,982,289 A * | 9/1976 | Robbins ................ 4/292 |
| 4,232,407 A | 11/1980 | Williams |
| 4,318,193 A | 3/1982 | Bayer et al. |
| 4,320,540 A | 3/1982 | Leavens |
| 4,361,279 A | 11/1982 | Beacham |
| 4,423,824 A | 1/1984 | Varndell |
| 4,505,429 A | 3/1985 | Mandon |
| 4,586,203 A | 5/1986 | Westgerdes |
| 4,706,306 A | 11/1987 | Smith |
| 5,165,118 A | 11/1992 | Cendrowski |
| 5,592,701 A | 1/1997 | Smith |
| 6,211,129 B1 * | 4/2001 | Gladfelter et al. ........ 510/294 |
| D441,848 S | 5/2001 | Huang |
| D454,177 S | 3/2002 | Tracy |
| D507,821 S | 7/2005 | Colpitts |
| D517,175 S | 3/2006 | Holsen |
| D517,664 S | 3/2006 | Hill |
| 7,013,500 B1 | 3/2006 | Lin |
| 2003/0176101 A1 | 9/2003 | Miller, Jr. |
| 2004/0073992 A1 | 4/2004 | Samen et al. |

OTHER PUBLICATIONS

PCT Notice of Transmittal of International Search Report, International Search Report and the Written Opinion of the International Searching Authority for PCT/US2006/016303 dated Aug. 31, 2007, 10 pgs.

* cited by examiner

*Primary Examiner*—Robert M Fetsuga
(74) *Attorney, Agent, or Firm*—Cook Alex Ltd.

(57) ABSTRACT

We provide a sink drain air freshener container that is generally used with sink cover or a sink strainer/stopper. The air freshener container contains a plastic-based air freshener that emits the fragrance for at least 20 days after being unwrapped and placed in use in a sink. The air freshener container has perforations to enable the container to be drained. The strainer/stopper is preferably made of disposable plastic and the container is preferably part of the top portion of the strainer/stopper stem that is used in conjunction with the strainer/stopper perforated basket.

7 Claims, 3 Drawing Sheets

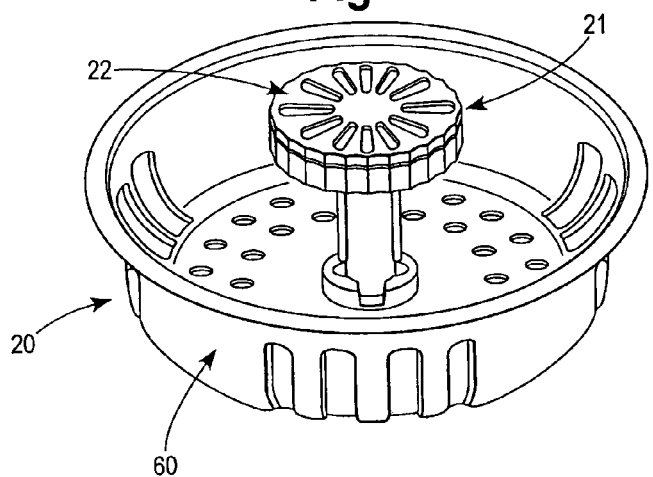
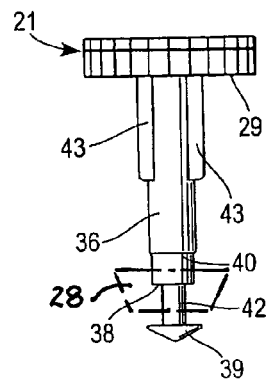
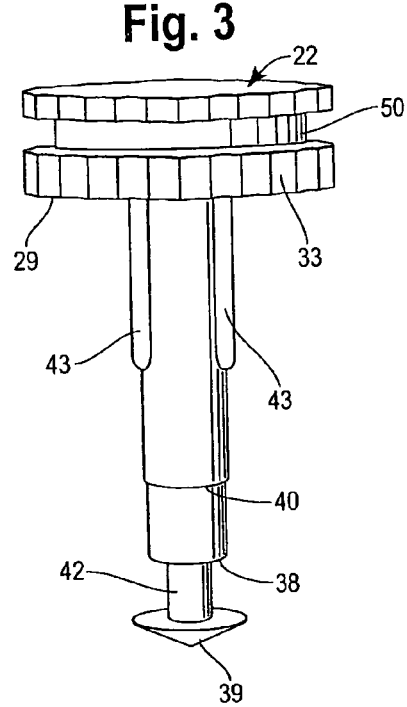
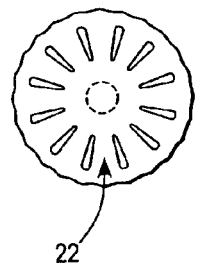
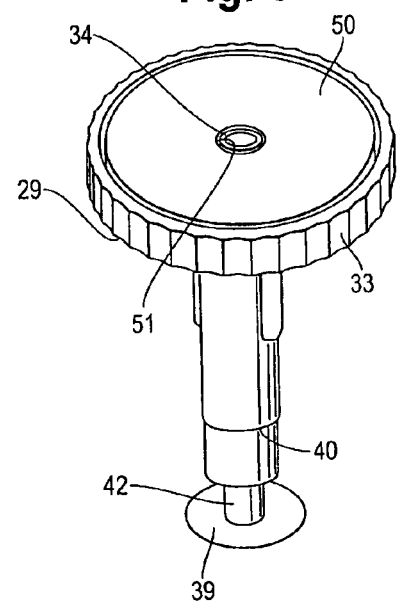

US 7,458,108 B2

SCENTED SINK STRAINER/STOPPER

BACKGROUND OF THE INVENTION

The present invention relates to an air freshener sink strainer/stopper and/or an air freshener strainer/stopper container.

DESCRIPTION OF RELATED ART

Presently sinks are deodorized by using a liquid air freshener that is applied by the user, or using a regular kitchen type air freshener or using a deodorant or air freshening ring that is generally connected the drain opening such as described in U.S. Pat. No. 4,318,193.

SUMMARY OF THE INVENTION

The present invention provides a sink drain air freshener container being able to be connected to a sink drain-cover or a strainer/stopper and the container has spaced walls defining an air freshener chamber and at least one of the walls has perforations.

The present invention further provides a sink drain air freshener container being able to be connected to a sink drain-cover or a strainer/stopper and the container is a perforated container and is sized to hold therein a shaped plastic-based air freshener that emits a fragrance for at least 20 days of use.

The present invention further provides for the ornamental design of the sink strainer/stopper and the air freshener strainer/stopper container as herein shown and defined.

The present invention further provides a sink strainer/stopper having a perforated basket and a strainer/stopper stem having an air freshener container at its upper end, the air freshener container having spaced upper and lower walls and a surrounding side wall defining and an air freshener chamber, a non-liquid plastic-based air freshener in said chamber, and at least one of the walls of the air freshener chamber is perforated.

The present invention still further provides a plastic air freshener sink strainer/stopper having a perforated basket, the perforated basket having a planar bottom wall, a side wall, a rounded wall joining the bottom wall and side wall, an outwardly extending lip at the opening of the basket, a stem guide extending upwardly from the center of the inner surface of the basket bottom wall, the stem guide has a central hole with a pair of diametrically opposed slots, the hole with its slots passes through the bottom wall, the guide also has diametrically opposed grooves which have groove bottom walls which are spaced above the bottom wall inner surface, a cylindrical stem having an appropriate length to raise and lower a sealing stopper in and out of a closing position, the stem having a handle that is attached to one end which is positioned in the basket inner surface above the inner surface of the bottom wall, a stopper holder to removably attach a stopper to the other end of the stem, the stopper and stem other end being positioned below the basket bottom wall, the stem handle is a cylindrical container having a scalloped side wall, a bottom wall centrally attached to the stem and having a plurality of radial extending slots, a cylindrical top wall closing the container and defining an air freshener chamber, the top wall having a plurality of radial extending slots, a flexible plastic-based cylindrical air freshener in said air freshener chamber, the stem having a pair of diametrically opposed ribs extending a predetermined distance from the bottom of the air freshener container to above the stopper and being sized to pass through the hole when the ribs are aligned with the hole slots and not to pass through the hole when they are not aligned, and said ribs being sized to fit into the guide grooves to hold the stopper in an open position.

BRIEF DESCRIPTION OF THE DRAWINGS

For a more complete understanding of the present invention and the advantages thereof, reference is now made to the following description and the accompanying drawings, in which:

FIG. 1 is a top perspective view of the strainer of the present invention.

FIG. 2 is a side perspective view of the stem of the present invention.

FIG. 3 is a side rear top perspective view of the stem of the present invention with the container cover separated.

FIG. 4 is a front view of the stem of FIG. 2.

FIG. 5 is a front side perspective view of the stem of FIG. 2 with the container cover removed.

DESCRIPTION OF THE PREFERRED EMBODIMENT

Figure 7:
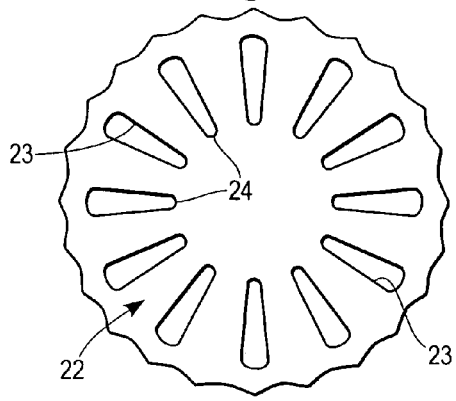
FIG. 7 is a top view of the container cover shown in FIG. 2.

Referring to FIGS. 1 and 7, the preferred embodiment is a sink strainer/stopper 20, having a vertically movable container/handle 21 that is used to open and close the strainer.

The container/handle 21 is a cylindrical container having a cylindrical top wall or cover 22. The cover 22 has a plurality radial extending slots 23. Preferably there are at least five slots 23 and the slots are equidistant from each other at their base 24.

Figure 6:
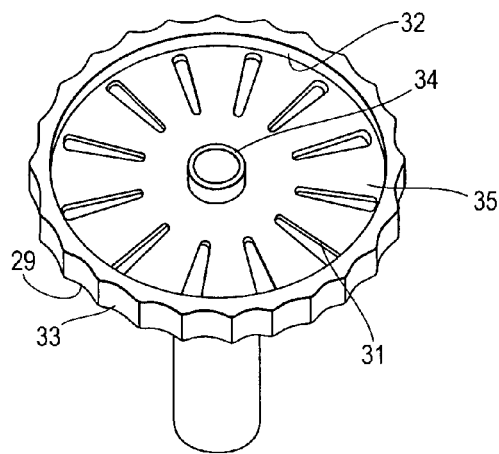
FIG. 6 is a front side perspective view of the stem of FIG. 5 with the air freshener removed.
Figure 8:
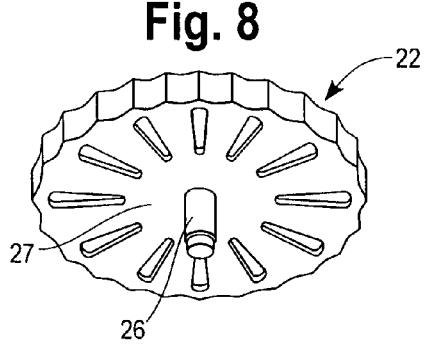
FIG. 8 is a bottom perspective view of the container cover.
Figure 9:
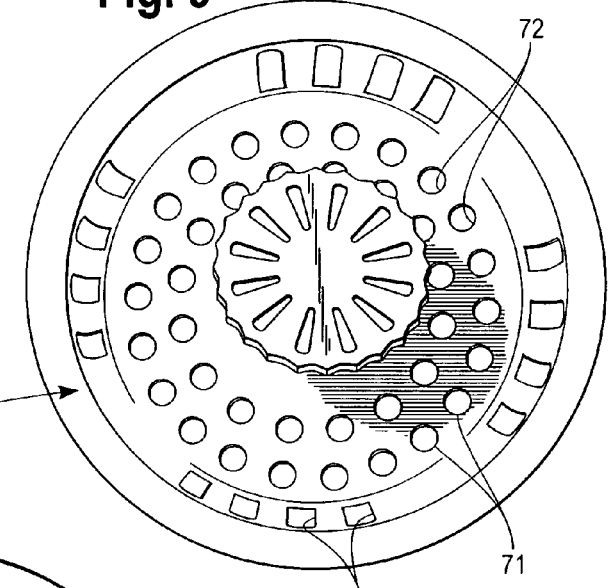
FIG. 9 is a top perspective view of the sink strainer of FIG. 1.
Figure 10:
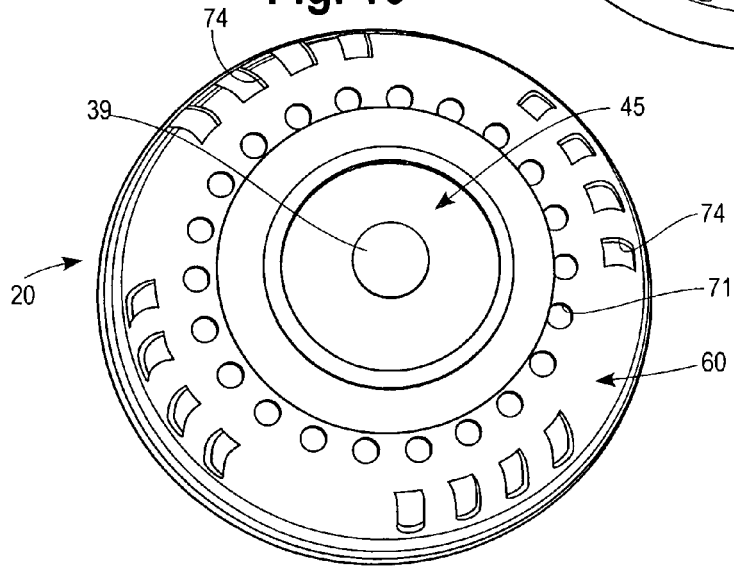
FIG. 10 is a bottom perspective view of the sink strainer of FIG. 1.
Figure 11:
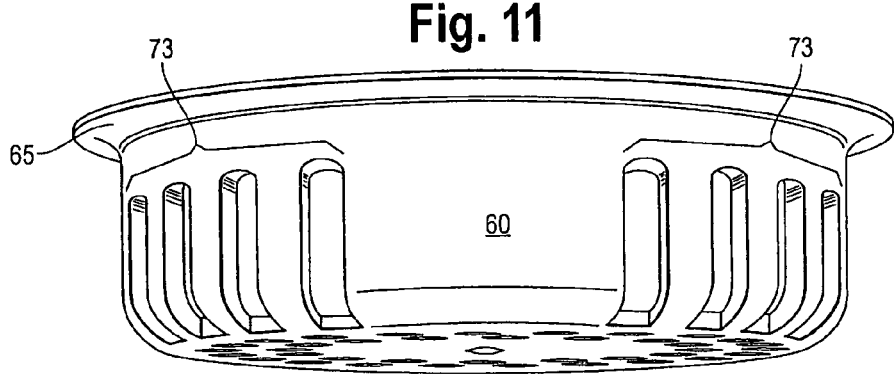
FIG. 11 is a side perspective view of the sink strainer of FIG. 1.
Figure 12:
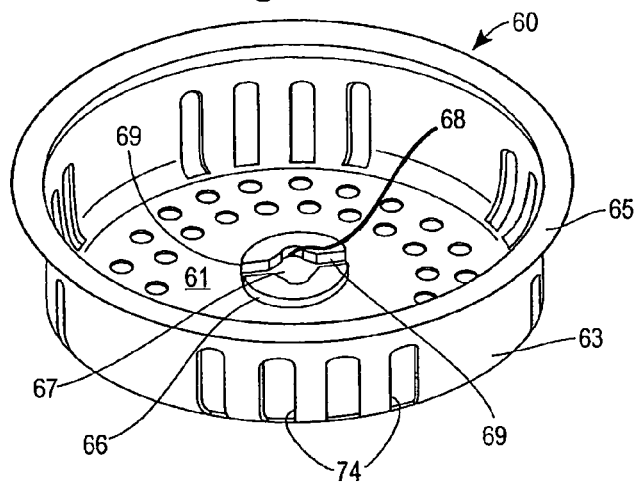
FIG. 12 is a top perspective view of the strainer basket of the strainer of FIG. 1.
Figure 14:
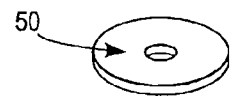
FIG. 14 is a top perspective of the air freshener of FIG. 5.
Figure 13:
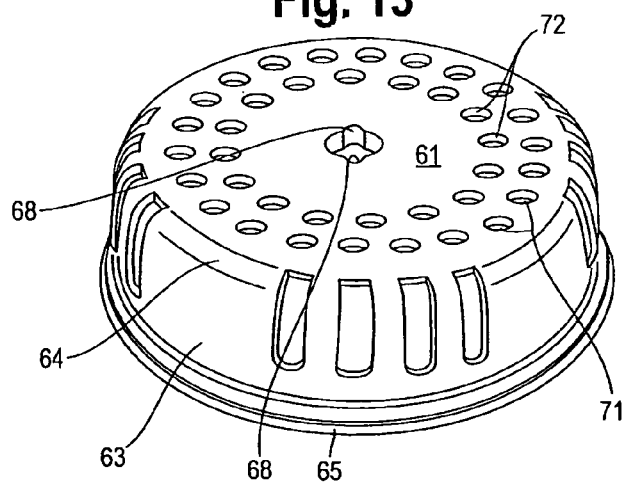
FIG. 13 is a bottom perspective view of the strainer basket of the strainer of FIG. 1.

Referring to FIGS. 1 and 8, the cover has an attachment rod 26 centrally extending from the inner surface 27 of the cover 22. The cover has a side that has a scalloped configuration. As shown in FIG. 6, the container bottom wall 29 is cylindrical and likewise has a plurality of radial extending slots 31. Preferably, there are at least five slots and the slots are equidistant from each other at their base. The container side wall 33 extends upwardly from the bottom wall 29 a predetermined distance. The side wall 33 has a scalloped configuration. A tubular extension 34 extends from the inner surface 35 of the bottom wall 29. The tubular extension 34 has a length substantially equal to the inner width of side wall 32. The attachment rod 26 has a diameter that allows the attachment rod to be press fitted into the tubular extension which extends a predetermined distance into the stem tubular body 36 and is preferably fixedly attached, i.e., by an appropriate adhesive.

As shown in FIG. 2, the container/handle 21 is attached to one end of the stem 36. The other end 38 of the stem has a holding mechanism to hold a sealing sink stopper 28 (depicted in broken lines). The sink stopper is preferably a non-odorous rubber or synthetic rubber. This is to prevent any odor from the stopper interfering with the pleasant fragrance of the scented sink strainer/stopper. The holding mechanism consists of a small circumferential ridge 40 spaced from the other end 38 and has a removable bottom cap 39 to hold the sealing stopper 28 on the other end of the stem. The bottom cap 39 has a central rod extension 42 that is press fitted into the stem to prevent the sealing stopper 28 from falling off the other end 38 of the stem.

The strainer/stopper stem has a pair of diametrically spaced ribs 43 that extend along the stem preferably from at or close to the outer surface of the bottom wall 29 a predetermined distance from. The ribs are one of the means that allow the sealing stopper to be in an open or closed position.

As shown in FIGS. 3 and 5, the air freshener 50 is preferably the shape of the container 21 and in this instance is a disk having a central hole 51 that allows the air freshener to surround the extension 34 and snuggly fit into the container. The width of the air freshener is substantially equal to the inner width of the container side wall 33.

The above stem, air freshener container and end caps are preferably made of molded plastic but if desired can be made from metal which is more expensive or can be a combination of metal and plastic. Also, the configuration of the cover and bottom wall may be reversed i.e. the cover would have side walls and be shaped as an open container and the bottom wall would be disk shaped. Also if desired, the top wall rod and bottom wall tube may be reversed.

The container bottom and cover outer side walls are scalloped to provide a better grip than would a smooth wall. However the configuration of the side walls are not an important feature of the invention and may have any configuration i.e. a rough surface, a knarled surface or even the less desirable smooth surface.

As shown in FIGS. 1 and 9-13, the sink strainer 20 has a perforated cylindrical basket 60. The perforated basket 60 has a perforated cylindrical planar bottom wall 61, a perforated cylindrical side wall 63, a perforated rounded wall 64 joining the bottom wall and side wall, and an outwardly extending lip 65 at the opening of the basket.

A tubular stem guide 66 extends upwardly from the center of the inner surface of the basket bottom wall. The stem guide has a central hole 67 with a pair of diametrically opposed slots 68. The hole and its guide slots pass through the basket bottom wall. The guide also has diametrically opposed grooves 69, which preferably end above the surface of the basket bottom wall.

The bottom wall has a first outer plurality of holes or perforations 71 forming an outer circle. There are at least 15 holes forming this outer circle. The bottom wall has a second inner plurality of holes or perforations 72 forming an inner circle which is concentric with the outer circle of perforations. The holes of the outer circle are the same size as the holes of the inner circle and there are at least 10 holes forming this inner circle. The side wall and rounded wall have four equal sets of perforations 73 with each perforation 74 having the same size and longitudinally extending from the bottom wall upwardly through the side wall and ending a predetermined distance from the open end of the side wall. Preferably each set of perforations have at least two perforations 74.

The bottom guide hole is sized to freely allow the stem to vertically pass through the hole when the stem ribs are aligned with hole slots. As noted above, the pair of diametrically opposed ribs extend a predetermined distance from the bottom of the air freshener container to above the stopper. The ribs and stem are sized to pass through the hole when the ribs are aligned with the hole slots. The ribs and stem do not to pass through the hole when they are not aligned and the ribs are sized to fit into the guide grooves to hold the stopper in an open position.

The strainer 20 is preferably disposable and is generally meant to be discarded when the air freshener is no longer effective. Therefore, the basket is preferably made of molded plastic. When the basket is made from metal, i.e., stainless steel, the handle and stem are made from plastic in that they are disposable. Also the stem and container can have any of the known configurations for sink strainer to allow the gasket or stopper to be placed into an open or closed position or to hold the cylindrical stopper onto the stem.

Figure 15:
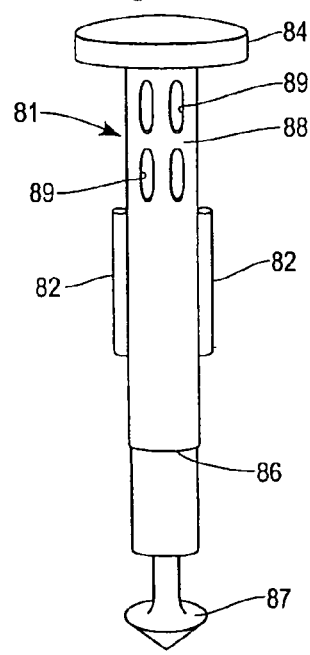
FIG. 15 is side view of an alternative strainer/stopper stem.

Referring to FIG. 15, there is shown an alternative strainer/stopper stem 81 having a pair of diametrically spaced ribs 82 that extend along the stem 81. The handle or strainer/stopper knob 84 is attached to one end of the stem. The other end of the stem has a holding mechanism to hold a sealing sink stopper. The holding mechanism consists of a small circumferential ridge 86 spaced from the other end and has a removable bottom cap 87 to hold the sealing stopper on the other end of the stem. The bottom cap has a central rod extension. The upper portion 88 of the stem acts as an air freshener container that uses the knob 84 as its cover. The upper portion of the container is hollow and preferably has a solid base at around the top of the ribs 82. The upper potion has a plurality of perforations 89 that allow for drainage. The air freshener (not shown) that fits in the upper portion is a cylindrical (rod) plastic-based air freshener. The upper perforated portion of the stem may have a different configuration or even telescope into the stem so as to provide a more compact package and that it is raised when in use.

I have shown the use of my invention on a sink strainer/stopper having a stopper, the sink strainer can be made with a fixed handle/container and be used as a garbage disposal cover.

The air freshener is a molded plastic based air freshener. Preferably, it is molded ethylene-vinyl acetate having the desired fragrance mixed with the plastic and then the combination molded or the fragrance infused into the molded plastic.

The fragrances I had used are lemon, apple cinnamon, Hawaiian Surf (tropical), Ocean Breeze(fresh and clean fragrance). However, any appropriate and plastic compatible non-toxic fragrance may be used. Preferably the sink strainer/stopper is disposable and foil wrapped to preserve its freshness. The scent container is manufactured with sufficient slots to allow water to drain out of the container. The plastic-based is manufactured to permit my sink strainer/stopper to remain effective for at least 20 days after it is removed from its foil wrapped package and placed into the sink.

Of course, other modifications than those discussed above may be used in producing a sink strainer without departing from the scope of the accompanying claims. Also unless limited by the prior art the term sink strainer is meant to cover any device which is to cover a sink drain whether or not the sink drain is connected to a garbage disposal.

The invention claimed is:

1. A sink drain air freshener stem and container constructed and arranged to connect to a sink drain strainer/stopper, comprising spaced top and bottom walls defining an air freshener container, said top and bottom walls having perforations, a plastic-based air freshener in said container, wherein the perforations in each of the bottom and top walls are at least five radial extending slots, and the top and bottom walls have cooperating attachments to attach the top wall to the bottom wall to provide the air freshener container, wherein the container is made of plastic and is disposable, and wherein the container is attached to a first end of a stem that is vertically movable in the sink drain strainer/stoppers, a second end of the stem being used to mount a flexible sink stopper, the top wall slots are equidistant from each other at their base, said container wall has an outer surface that has a scalloped configuration, and said strainer stem has means to hold the sink stopper in an open position.

2. The sink drain air freshener container of claim 1, wherein the container is cylindrical and the air freshener has a substantially disk shape and is configured to fit in the container, and the container has a cylindrical side wall with an outer surface that is configured to allow easy hand gripping.

3. The sink drain air freshener container of claim 1, wherein the air freshener is a disk shaped flexible molded ethylene vinyl acetate polymer and fragrance combination that emits the fragrance for at least 20 days after being unwrapped and placed in use in a sink.

4. A sink strainer/stopper having a perforated basket comprising:
- a stem having an air freshener container at its upper end, said air freshener container having an upper wall and a lower wall spaced from the upper wall and a surrounding side wall, the upper, lower and side walls defining the air freshener container, a non-liquid plastic-based air freshener in said container, at least one of the air freshener container walls having perforations, wherein the container is cylindrical, the air freshener has a substantially disk shape and is configured to fit in the air freshener container, said side wall is cylindrical with an outer surface that is configured to allow easy hand gripping, said container is attached to a first end of the stem, a second end of the stem being used to mount a flexible stopper, the wall perforations are radial extending slots that are equidistant from each other at their base, and said stem has means to hold the stopper in an open position.

5. The sink strainer/stopper of claim 4, wherein the stem and container are plastic, the container is cylindrical, and the air freshener is configured to fit in the container.

6. The sink strainer of claim 4, wherein the container side wall outer surface has a scalloped configuration, the perforations that are radial extending slots equidistant from each other at their base are in both the top wall and the bottom wall, and the air freshener is a disk shaped flexible molded ethylene vinyl acetate polymer and fragrance combination that emits the fragrance for at least 20 days after being unwrapped and placed in use in a sink.

7. A plastic air freshener sink strainer/stopper comprising:
- a perforated basket, the perforated basket having a planar bottom wall, a side wall, a rounded wall joining the bottom wall and side wall, an outwardly extending lip at the opening of the basket,
- a stem guide extending upwardly from the center of the inner surface of the basket bottom wall, said stem guide having a central hole with a pair of diametrically opposed slots, said hole with its slots passing through the bottom wall, the guide also has diametrically opposed grooves which are spaced above the bottom wall inner surface,
- a cylindrical stem having an appropriate length to raise and lower a sealing stopper in and out of a closing position, the stem having a handle that is attached to one end which is positioned in the basket inner surface above the inner surface of the bottom wall, a stopper holder to removably attach a stopper to the other end of the stem,
- said stopper and stem other end being positioned below the basket bottom wall,
- said stem handle is a cylindrical container having a scalloped side wall, a bottom wall centrally attached to the stem and having a plurality of radial extending slots, a cylindrical top wall closing the container and defining an air freshener chamber,
- said top wall having a plurality of radial extending slots,
- a flexible plastic-based cylindrical air freshener in said air freshener chamber, and
- said stem having a pair of diametrically opposed ribs extending a predetermined distance from the bottom of the air freshener container to above the stopper and being sized to pass through the hole when the ribs are aligned with the hole slots and not to pass through the hole when they are not aligned, and said ribs being sized to fit into the guide grooves to hold the stopper in an open position.

* * * * *